(12) United States Patent
Hautcoeur et al.

(10) Patent No.: US 11,344,425 B2
(45) Date of Patent: May 31, 2022

(54) VERTEBRAL SPACER

(71) Applicants: Nimesis Technology, Mecleuves (FR); Jean-Luc Chauvin, Montboucher sur Jabron (FR); Thierry Bourlon, Marseilles (FR)

(72) Inventors: Alain Hautcoeur, Mecleuves (FR); Florian Fouche, Mecleuves (FR)

(73) Assignees: Nimesis Technology, Mecleuves (FR); Jean-Luc Chauvin, Montboucher sur Jabron (FR); Thierry Bourlon, Marseilles (FR)

( * ) Notice: Subject to any disclaimer, the term of this patent is extended or adjusted under 35 U.S.C. 154(b) by 38 days.

(21) Appl. No.: 16/361,550

(22) Filed: Mar. 22, 2019

(65) Prior Publication Data
US 2020/0297508 A1    Sep. 24, 2020

(51) Int. Cl.
*A61F 2/44*    (2006.01)
*A61F 2/30*    (2006.01)

(52) U.S. Cl.
CPC .. *A61F 2/4425* (2013.01); *A61F 2002/30092* (2013.01); *A61F 2002/30433* (2013.01); *A61F 2002/30476* (2013.01); *A61F 2002/443* (2013.01)

(58) Field of Classification Search
CPC .......... A61F 2/4425; A61F 2002/30438; A61F 2002/443
See application file for complete search history.

(56) References Cited

U.S. PATENT DOCUMENTS

| | | | |
|---|---|---|---|
| 5,171,278 A | 12/1992 | Pisharodi | |
| 5,549,679 A | 8/1996 | Kuslich | |
| 5,972,015 A | 10/1999 | Scribner et al. | |
| 6,676,665 B2 | 1/2004 | Foley et al. | |
| 8,007,508 B2* | 8/2011 | Cox | A61B 17/320016 606/198 |
| 9,089,347 B2* | 7/2015 | Sankaran | A61B 17/1617 |
| 9,980,715 B2* | 5/2018 | Marino | A61B 17/0401 |

(Continued)

FOREIGN PATENT DOCUMENTS

| FR | 3 008 301 | 1/2015 |
|---|---|---|
| WO | WO 2005/048856 | 6/2005 |

OTHER PUBLICATIONS

International Search Report and Written Opinion Issued in PCT/EP2020/057856 dated Jun. 30, 2020.

*Primary Examiner* — Anu Ramana
(74) *Attorney, Agent, or Firm* — DLA Piper LLP (US)

(57) ABSTRACT

The present invention relates to a spacer intended to be introduced between two elements of a vertebral body. This spacer comprises a tube, a spacer module and an actuating system of the spacer module, the actuating system comprising at least one rod which is, on one hand, accessible from a distal end of the tube and, on the other hand, connected to said spacer module. The spacer is characterized in that the spacer module comprises two blades coplanar to a longitudinal axis of the rod, these blades being movable between a closed position in which the blades are substantially parallel to the longitudinal axis of the rod, and a deployed position in which the blades have an arched shape, and in that in their deployed position, these blades are asymmetrical with respect to each other and with respect to said longitudinal axis of the rod.

20 Claims, 4 Drawing Sheets

(56) References Cited

U.S. PATENT DOCUMENTS

| | | | |
|---|---|---|---|
| 10,022,132 B2 * | 7/2018 | Wlodarski | A61B 17/1617 |
| 10,028,840 B2 * | 7/2018 | Schaller | A61B 17/8852 |
| 10,076,342 B2 * | 9/2018 | Wlodarski | A61B 17/1617 |
| 10,219,851 B1 * | 3/2019 | Messerli | A61B 17/8858 |
| 2002/0026197 A1 | 2/2002 | Foley et al. | |
| 2002/0072768 A1 * | 6/2002 | Ginn | A61B 34/76 |
| | | | 606/213 |
| 2004/0153064 A1 * | 8/2004 | Foley | A61B 17/8858 |
| | | | 606/53 |
| 2006/0100706 A1 | 5/2006 | Shadduck et al. | |
| 2007/0198013 A1 | 8/2007 | Foley et al. | |
| 2008/0071356 A1 | 3/2008 | Greenhalgh et al. | |
| 2009/0299378 A1 | 12/2009 | Knopp | |
| 2010/0217335 A1 | 8/2010 | Chirico et al. | |
| 2015/0230848 A1 | 8/2015 | Chirico et al. | |
| 2016/0317188 A1 | 11/2016 | Oglaza et al. | |

\* cited by examiner

VERTEBRAL SPACER

TECHNICAL FIELD

The present invention relates generally to the field of surgery and applies in particular to the field of reconstructive surgery for vertebral fractures or for vertebroplasty.

In more detail, this invention relates to a spacer for insertion into the vertebral body of a patient. In particular, this spacer is intended to be introduced between two parts of a vertebra and in particular between two parts of a fractured or otherwise defective vertebra.

BACKGROUND ART

Vertebral fractures are a relatively common condition that can occur as a result of a fall or an accident, but in most cases occur as a result of osteoporosis.

One way to treat these fractures is the use of vertebroplasty or kyphoplasty. This technique consists in injecting a consolidation material such as a resin, an acrylic cement or, more generally, a biocompatible fluid material, hardening after injection, into the fractured or defective vertebra in order to consolidate it. Before the injection of the consolidation material, the two parts or endplates of the fractured or defective vertebra can ideally be spaced relative to each other by means of a spacer, so as to minimize the settlement due for example to the fracture or osteoporosis and to restore the vertebra to its original shape. The spacer is inserted into the vertebra to be treated, between the vertebral plates, and is then actuated so that the two plates are moved to the desired position. A consolidation material is then introduced by means of a trocar into the space generated by the spacer, so as to stabilize the plates of the vertebra in the desired position.

There are currently several types of spacers suitable for reconstructive surgery of fractured or defective vertebrae. These spacers, however, all have certain disadvantages.

The publications FR 3,008,301, U.S. Pat. No. 5,171,278, US 2016/0317188 and WO 2005/048856 disclose spacers in the form of "mini jacks" provided with plates which can be moved by means of a toothed or threaded rod.

Given the size of the components of these spacers and the size of the vertebrae in which these spacers are introduced, the realization of these mini jacks is extremely delicate. This generates high manufacturing costs. In addition, during actual use, the spacer is introduced into the pedicle of the vertebra by means of a tube or a trocar. Manipulation of the handle, placed outside of the patient, makes it possible to modify the spacing of the plates placed inside the patient during use of the spacer. This means that the spacer is generally introduced at a non-zero angle relative to the vertebral plates. This angle can be of the order of 20° to 30°. The plates of these jacks are aligned with the trocar and thus form an angle of 20° to 30° with respect to the vertebral plates. The plates of the jacks then tend to position themselves at an angle to the desired position. They are then no longer able to position the parts of the vertebra adequately and/or they deform.

More generally, it is difficult to position these jacks correctly. Once they are placed in the vertebra, it is no longer possible to change their position. Thus, it is difficult to control the displacement of the vertebral plates, meaning that such displacement is generally not optimal. Moreover, a substantial force is required to properly position the vertebral plates. Small jacks are not suitable in the presence of such forces and the risk of breakage of some parts cannot be excluded.

Other spacers, for example those described in U.S. Pat. No. 5,549,679 and U.S. Pat. No. 5,972,015, are provided with an inflatable element. This inflatable element takes the form of the cavity in which it is introduced. As a result, it is not possible to move the plates of the vertebra into a chosen position. The position after displacement depends on the shape and the forces applyied to the vertebra, without the surgeon having any possibility to control this shape and these forces.

Publication US 2006/0100706 describes a stent-type, spherical spacer. Because of this spherical shape, the shape of the spacer and the forces it applies to the vertebrae parts to be moved do not depend on its position in the vertebra, since in all cases it has the shape of a sphere.

These different spacers do not allow for a force to be applied in a chosen direction, neither is their construction simple or robust.

BRIEF SUMMARY OF THE INVENTION

The present invention provides for a spacer intended to be implanted in the vertebral body of a patient, in particular between the plates of a vertebra, while at the same time making it possible to control the displacement of the vertebral plates with regard to both the amplitude and direction of the displacement. In addition, the proposed spacer is of simple construction and can be positioned and used relatively easily. This spacer also allows for different treatments for anterior and posterior fractures, and this in a simple manner.

This spacer is adapted to the conditions of use commonly encountered in practice, especially with regard to the forces which need to be applied to move the vertebral plates to the desired position. The spacer is also adapted for introduction into a pedicle of a vertebra, at a non-zero angle with respect to the plates of the vertebra.

The object of the invention is achieved by a spacer intended to be introduced between two elements of a vertebral body, the spacer comprising a tube, a spacer module and an actuating system of the spacer module, the actuating system comprising at least one rod, on one hand accessible from a distal end of the tube and, on the other hand, connected to said spacer module, this spacer being characterized in that the spacer module comprises two blades coplanar to a longitudinal axis of the rod, these blades being movable between a closed position in which the blades are substantially parallel to the longitudinal axis of the rod, and a deployed position in which the blades have an arched shape, and in that in their deployed position, these blades are asymmetrical with respect to each other and with respect to said longitudinal axis of the rod.

The spacer according to the present invention is of simple and robust construction. It does not have complex moving pieces, which allows for a small size spacer, without it being fragile. This is very advantageous because the spacer must be introduced into a vertebra of the patient through a tube having a dimension as small as possible.

This spacer can easily be positioned in an orientation chosen by the surgeon according to the morphology or the pathology of the patient, so as to be placed in the optimal position. In addition, the spacer can be repositioned, if necessary, before the injection of the consolidation material.

This spacer is particularly interesting in that it allows for the plates of the vertebrae to be moved according to a force and a direction chosen by the surgeon, which allows for the vertebral plates to be placed, for example, in substantially parallel planes to one other. This can be particularly difficult with the spacers of the prior art. The spacer of the invention allows, in particular, for a precise and controlled adjustment of the opening of the spacer.

BRIEF DESCRITPION OF THE DRAWINGS

The present invention and its advantages will be better understood with reference to the enclosed drawings and the detailed description of particular embodiments, in which.

DETAILED DESCRIPTION

Figure 1:
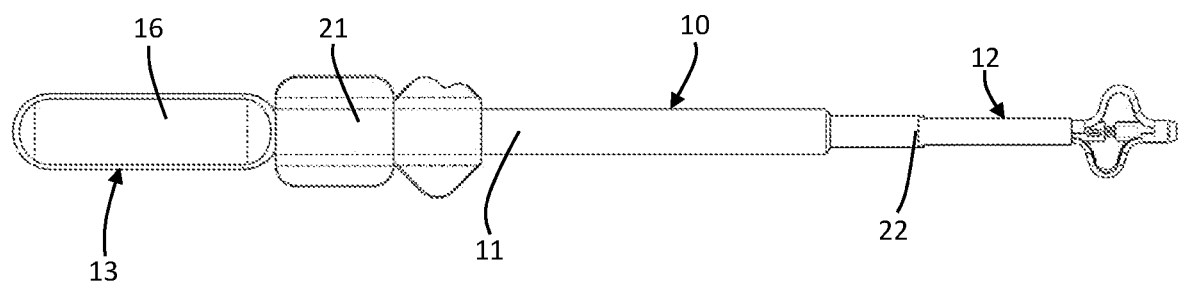
FIG. 1 is an overall view of a first embodiment of a spacer according to the present invention.
Figure 2:
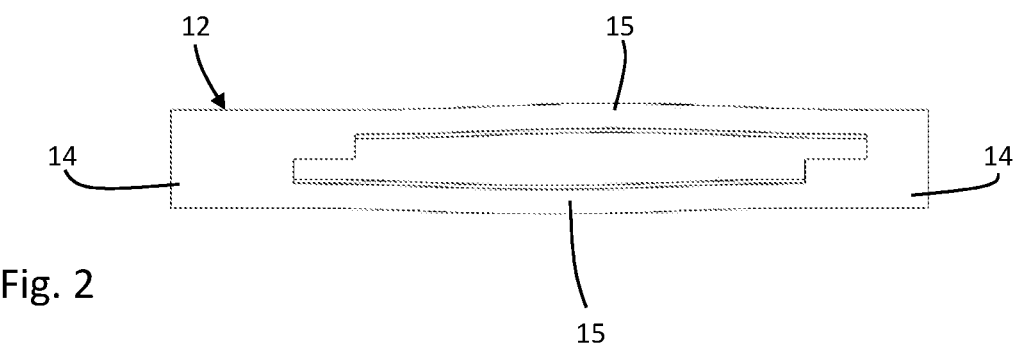
FIG. 2 is a view of a spacer module used in the spacer of FIG. 1, the spacer module being in a closed position.
Figure 3:
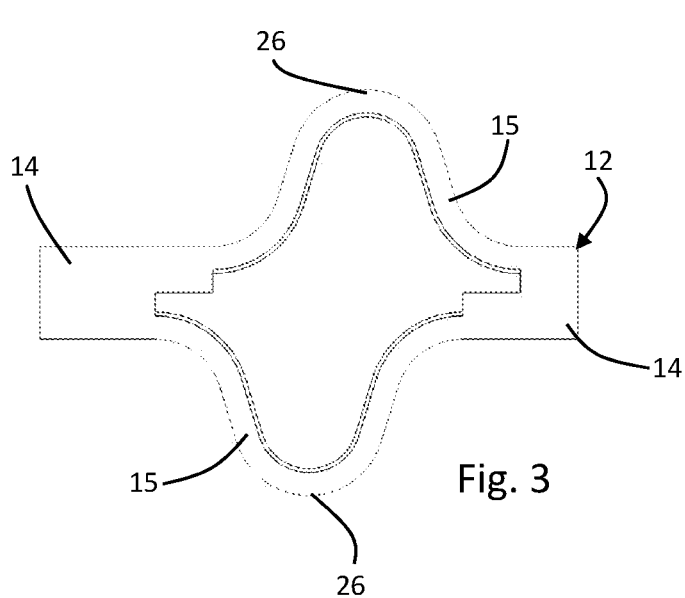
FIG. 3 is a side view of the spacer module of FIG. 2, in a deployed position.
Figure 4:
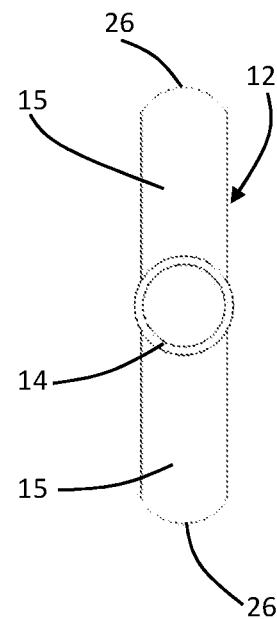
FIG. 4 is a front view of the spacer module of FIG. 3.

With reference to the drawings, the spacer 10 according to the present invention essentially comprises a tube 11, a spacer module 12 and an actuating system 13 of the spacer module.

In general, the spacer module 12 and the actuating system 13 are arranged at least partially within the tube 11. The actuating system 13, when actuated, is configured to move the spacer module 12 when the tube 11 is placed in a patient who has to undergo a vertebroplasty operation. This actuating system 13 can be actuated from outside of the patient's body and acts on the spacer module 12 which is inside the patient's body.

Referring to FIGS. 1 to 8, corresponding to a first embodiment of the spacer of the invention, the spacer module 12 according to the present invention has a substantially tubular shape. This spacer module 12 comprises a holding zone 14 at each of its ends and two blades 15 integral with these holding zones 14. The holding zone farthest from the end of the tube remaining outside of the patient during a vertebroplasty operation is referred to as a proximal holding zone 14a, the opposed holding zone being referred to as a distal holding zone 14b. The blades 15 have a certain flexibility so that the holding zones 14 can be brought together or moved apart from one another, this having the effect of modifying the shape of the blades, as can be seen for example in FIG. 3 and as explained in more detail below.

According to a particular embodiment of the spacer module 12, the latter is made in a partially perforated cylinder so that the blades 15 and the holding zones 14 are made in one piece. According to one variant, the blades 15 are made separately from the holding zones 14 and are then fixed to these holding zones. This fixing can for example be done by means of a core (not shown) placed inside the holding zones, integral both with the holding zones 14 and the blades 15.

These different embodiments make it possible, for example, to have either identical or different materials for the blades and for the holding zones. It is also possible to use additive manufacturing techniques which also make it possible to have identical or different materials for different parts of the spacer module.

The blades 15 of the spacer module are asymmetrical with respect to any axis perpendicular to a longitudinal axis of the tube, as explained in more detail below.

The actuating system 13 of the embodiment illustrated in FIGS. 1 to 8 is at least partially visible, in particular in FIGS. 1 and 5 to 8. This actuating system comprises a handle 16 connected to a rod 17 having one threaded proximal end 18 and a nut 19 having an internal thread cooperating with the threaded proximal end 18 of the rod 17.

The nut 19 is integral with the spacer module 12. According to a variant, this nut 19 is introduced into the proximal holding zone 14a of the spacer module 12 and is fixed to this holding zone, for example by a screw. According to another variant, the blades 15 are integral with the nut 19 and are fixed to this nut, for example by screwing or by a housing formed in the periphery of the nut. A part of the nut 19 can form one of the holding zones of the spacer module 12.

The rod 17 of the actuating system 13, and more particularly, the threaded end 18 of this rod can move within the nut 19. This rod 17 rotates inside the tube 11 and inside the module. This rod 17 has a shoulder 20 against which the distal holding zone 14b of the spacer module 12 bears.

The rotation of the handle 16 has the effect of rotating the rod 17, which causes a longitudinal displacement of the nut 19. As the spacer module 12 and thus the blades 15 are held between the nut 19 and the shoulder 20 of the rod, the modification of the distance between the nut 19 and this shoulder 20 has the effect of bringing the holding zones 14a, 14b either closer from each other or away from each other and, consequently, of modifying the shape of the blades 15. For this purpose, the travel or stroke of the rod 17 in the nut 19 must be such that the blades 15 can reach the extreme positions provided for these blades.

Figure 5:
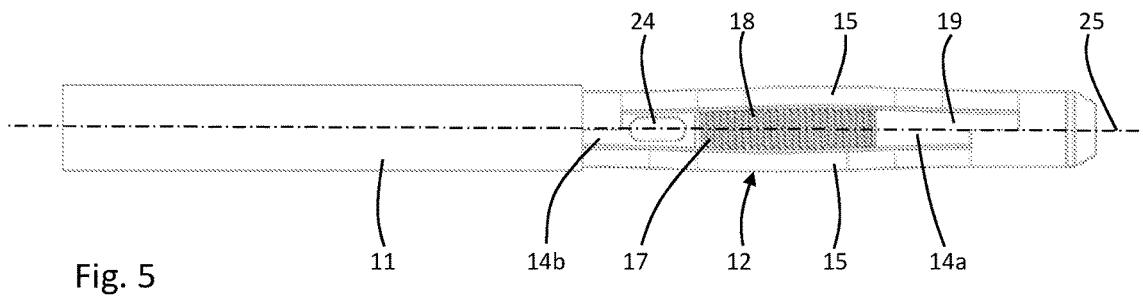
FIG. 5 is a view of a proximal end of the spacer of FIG. 1 in the closed position.

In FIG. 5, the blades 15 are in a closed position and the threaded proximal end 18 of the rod 17 is introduced as little as possible into the nut 19. This threaded end 18, however, always includes a zone contained in the nut 19. In the closed position, the blades are slightly curved so that, when the holding zones are approached, these blades are deformed and deviate from one another in an extension direction.

Figure 6:
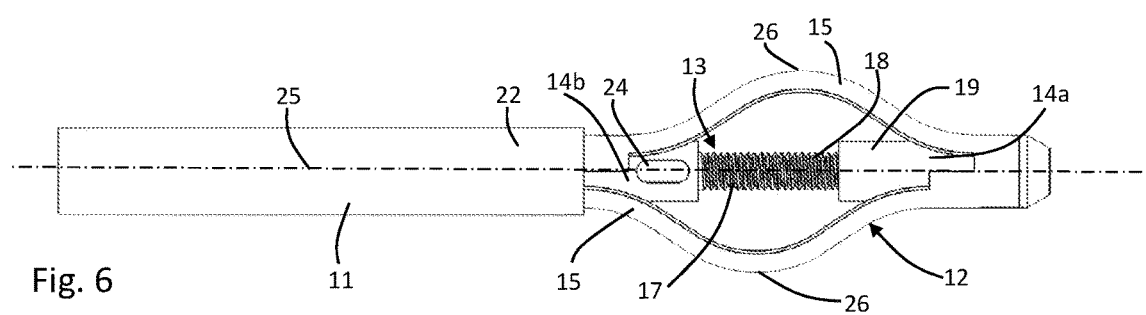
FIG. 6 is a view similar to FIG. 5, the blades being in a partially deployed position.

In the position illustrated in FIG. 6, the spacer module 12 is partially outside of the tube 11. The threaded proximal end 18 of the rod 17 is inserted into the nut 19 over a distance, this distance being greater than the distance shown in FIG. 5. The blades are in a more arched position than in the configuration of FIG. 5 and correspond to a partially deployed position.

Figure 7:
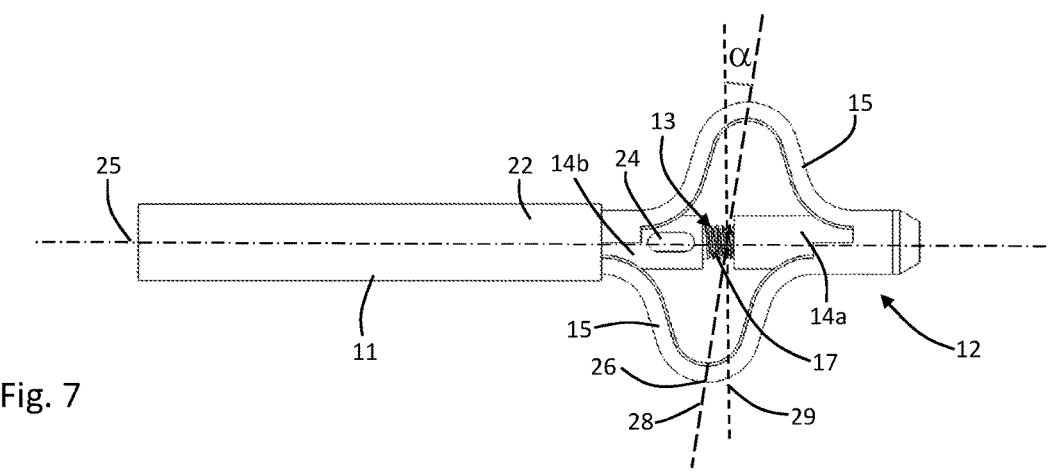
FIG. 7 is a view similar to FIG. 5, the blades being in a fully deployed position.
Figure 8:
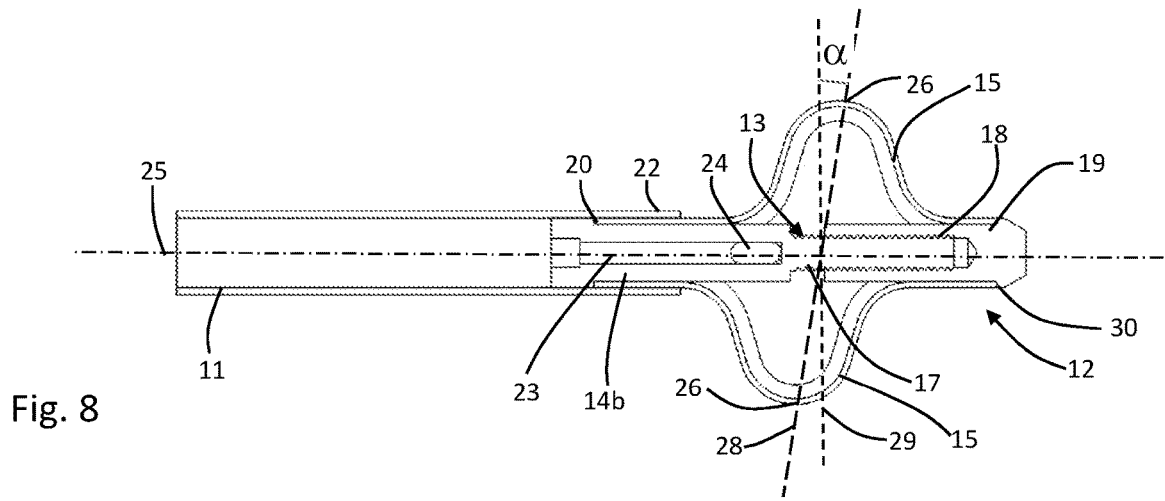
FIG. 8 is a sectional view of one end of the spacer of FIG. 1, the blades being in the position illustrated in FIG. 7.
Figure 9:
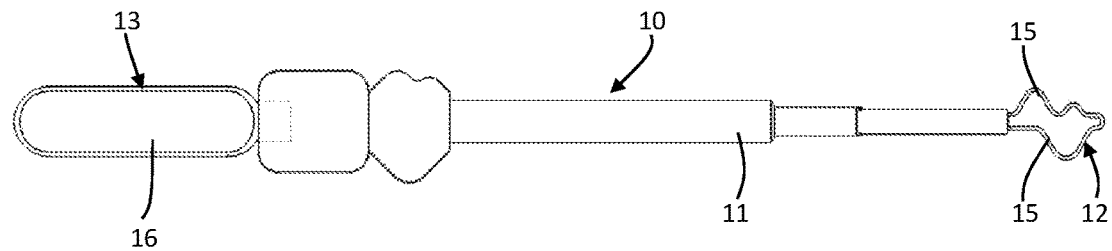
FIG. 9 is an overall view of a second embodiment of a spacer according to the present invention.

In the position illustrated in FIGS. 7 and 8, the threaded proximal end 18 of the rod 17 is introduced into the nut 19 over a distance as great as possible, which has the effect that the distance between the shoulder 20 of this rod and the nut 19 is as short as possible. In this configuration, the blades 15 are in an extended, or deployed, position.

Manipulation of the handle 16 placed outside of the patient thus makes it possible to modify the opening or the spacing of the blades 15 disposed inside the patient when the spacer 10 is used.

The tube 11 is hollow and has a distal end 21 intended to remain outside the patient's body when the spacer 10 is used, and a proximal end 22 intended to be placed near the vertebra when this tube 11 is in place for a vertebroplasty operation. This tube 11 has an inner diameter such that it is able to receive the spacer module 12 and a part of the actuating system 13. This tube 11, as well as the rod 17 of the actuating system, can have some flexibility. This flexibility contributes to the correct positioning of the spacer in the vertebra.

According to an advantageous embodiment, the nut 19 comprises a shoulder 30 against which is placed the proximal holding zone 14a of the spacer module 12. This nut 19 comprises a rounded or chamfered zone so that the nut 19 and the spacer module 12 do not have sharp angles that can cause damage or injury when they are placed internal to a patient.

The rod 17 comprises a channel 23 opening into the tube 11 of the spacer on one hand and, on the other hand, opening into a opening 24 provided in this rod near the blades 15.

As previously mentioned, the blades 15 can be deformed between two distinct end positions. In a first position, illustrated in FIG. 5, the blades 15 are substantially rectilinear and substantially parallel to a longitudinal axis 25 of the rod 17. In this position, the nut 19 is in a position as far as possible from the shoulder 20 of the stem.

In a second position illustrated in FIG. 6, the blades 15 have a zone distant from the rod 17 and have an arched shape. The threaded end 18 of the rod is retracted a greater distance into the nut 19 so that the nut 19 is closer to the shoulder 20 of the rod than when the blades are in the closed position. In this configuration, the blades 15 are said in the partially deployed position.

In a third position illustrated in FIGS. 7 and 8, the threaded end 18 of the rod is retracted an even greater distance into the nut 19 so that the nut 19 is even closer to the shoulder 20 of the rod. In this configuration, the blades 15 are said in the deployed position.

In these deployed or partially deployed configurations, each of the blades 15 has an arc or bending curve. The bending curve may comprise an apex 26 or peak, defined by the furthest point of a longitudinal axis 25 of the rod or defined by an area having a tangent parallel to the longitudinal axis 25 of the rod.

Figure 13:
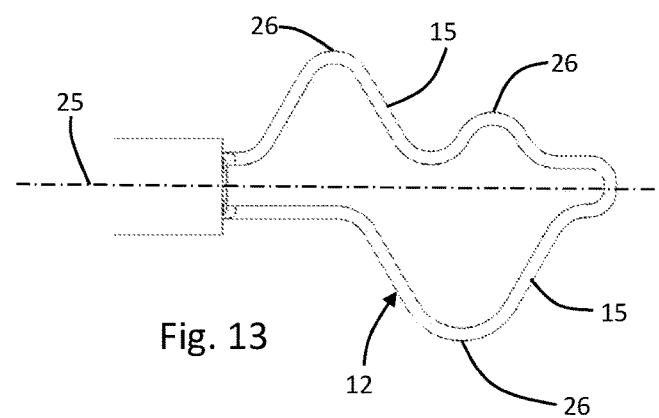
FIG. 13 is a profile view of a spacer module in which spacer blades comprise two apexes.

The bending curve may comprise several apexes 26, as shown in FIG. 13, the apexes being defined by the points of this curve for which the tangents are parallel to the longitudinal axis 25 of the rod.

Figure 14:
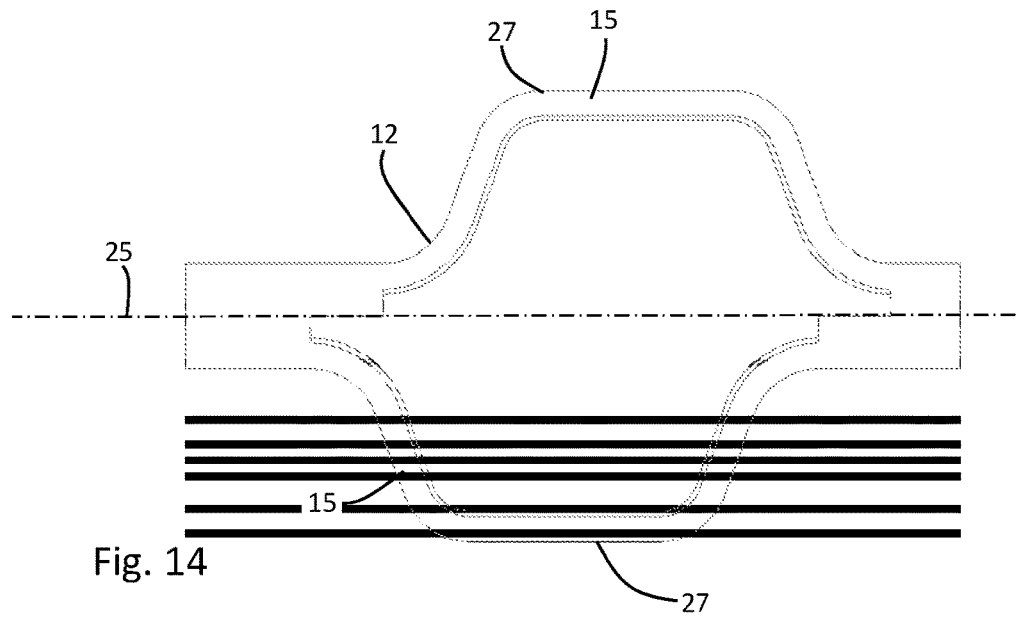
FIG. 14 illustrates a spacer module in which the blades have a rectilinear peak zone when they are in the deployed position.

The bending curve may comprise an apex zone 27, namely a rectilinear zone parallel to the longitudinal axis 25 of the rod 17 and whose distance to the rod is maximum when the blades are in a deployed position. Such an embodiment is illustrated in FIG. 14.

In embodiments wherein each blade has a single apex 26 when the blades are in the deployed position, the apexes of each of the blades are offset along the longitudinal axis of the rod such that a plane perpendicular to this longitudinal axis 25 and containing the apex 26 of one of the blades 15 is distinct from the plane perpendicular to the longitudinal axis 25 of the rod and containing the apex of the other blade. The planes containing the apex of each of the elastic blades are distinct, or the blades are asymmetrical with respect to the longitudinal axis of the rod.

In the case where at least one of the blades has more than one apex, as illustrated in FIG. 13, it is possible that a plane perpendicular to the longitudinal axis of the tube containing an apex of a blade also contains an apex of the other blade. However, even in this case, the blades are asymmetrical with respect to the longitudinal axis of the rod. This is also true in a case where at least one of the blades comprises an apex zone 27, as illustrated by FIG. 14.

It is possible to draw a line 28 connecting the apexes 26 of the blades. This line 28 forms an angle α with a plane 29 perpendicular to the longitudinal axis 25 of the rod. This angle α can be between 5° and 45°. Preferably, this angle is between 10° and 30°. In the preferred embodiment, the angle is between 15° and 25°. In this way, if we consider that the vertebral plates are horizontal and that the spacer is introduced at an angle of the order of 20°, the line 28 connecting the apexes of the blades will be substantially vertical and the vertebral plates will undergo a force in a substantially vertical direction.

Depending on the embodiment, it is possible that the two blades 15 have an identical general shape. In this case, they are offset along the longitudinal axis 25 of the rod so as to be asymmetrical with respect to this longitudinal axis 25. The offset may be such that the angle between equivalent points of the blades forms an angle α between 5° and 45° with respect to a plane perpendicular to the longitudinal axis 25 of the rod. As mentioned above, this angle is preferably between 10° and 30° and ideally between 15° and 25°.

The arched shape of the blades 15 can be obtained in several ways. In a first way, the blades 15 are made of an elastic material and their shape is given mechanically, by the combination of the nut 19 and the threaded rod 17.

In a second way, the blades 15 are prestressed so as to have an arched shape in the absence of external stress, or pressure. Such prestressing can be performed during the manufacture of the blades.

According to another embodiment, these blades 15 are made of a shape memory alloy and can be deformed between two distinct shapes. In a first shape, corresponding to a martensitic phase, the blades 15 are substantially rectilinear. In a second shape, corresponding to an austenitic phase of the shape memory alloy, the blades 15 have an arched shape.

According to one embodiment, the shape memory alloy is designed in such a way that the transition temperature between the martensitic and austenitic phases is preferably between room temperature and the temperature of the human body. At room temperature, the blades are in a martensitic phase and remain close to the rod 17 in a closed position. When they reach the temperature of the human body, the blades are in austenitic phase and tend to deviate from this rod 17 to take on a deployed position.

The room temperature can be considered as a temperature between 20° C. and 25° C. The temperature of the human body can be considered to be greater than or equal to about 36.5° C.

In another embodiment, the shape memory alloy is a conventional alloy such as Nitinol. The alloy is in a martensitic phase when it is at a low temperature, typically below 10° C. This alloy is in the austenitic phase when it is introduced into the human body, at a temperature close to 37° C.

FIGS. 9 to 13 illustrate an embodiment of a spacer 10 according to the invention, wherein the actuating system 13 does not include a nut. In this embodiment, the blades 15 are prestressed so that in the absence of external stress on the blades, they take on a deployed position. This prestressing can be given by mechanical stress during the manufacture of the blades or after this manufacture. The stress can also be given by the use of a shape memory alloy, the deployed shape of the blades being given when the alloy is in the austenitic phase.

In the illustrated example, the blades 15 are formed in one piece, the two ends of the blades being arranged side by side and being held on a fastener element 31 of the blades. This fastener element 31 is movable within the tube 11 so as to allow the blades to be moved from a position within the tube to a position where the blades 15 protrude from this tube. This fastener element is connected to the rod 17, the displacement of the rod 17 generating a displacement of the fastener element 31 and blades 15.

Figure 10:
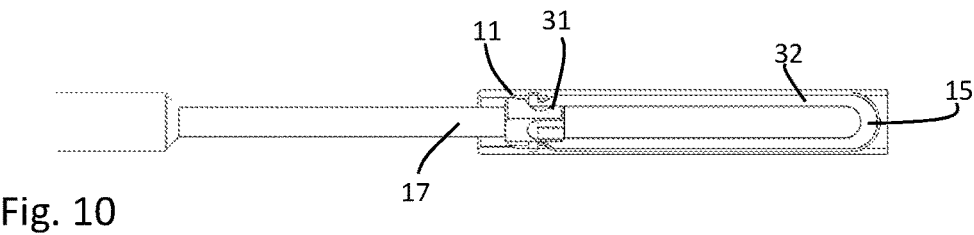
FIG. 10 is a sectional view of a spacer module that can be used in the spacer of FIG. 9, this spacer module being in a closed position.
Figure 11:
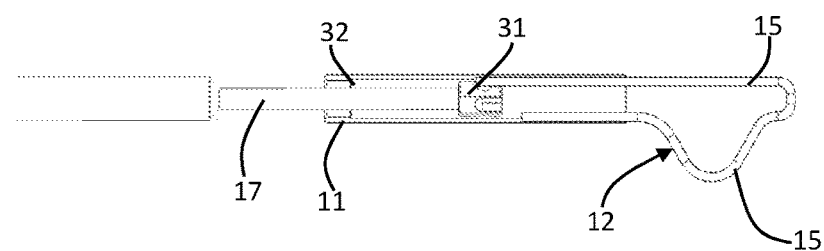
FIG. 11 is a sectional view of the spacer module of FIG. 10, in a partially deployed position.
Figure 12:
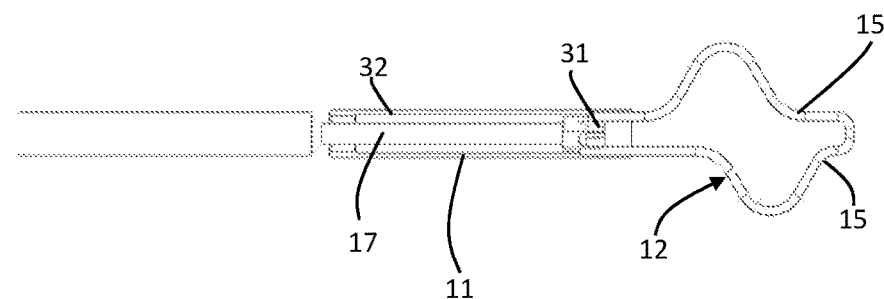
FIG. 12 is a sectional view of the spacer module of FIG. 10, in a deployed position.

FIG. 10 illustrates the position and shape of the blades 15 when fully disposed within the tube 11. The blades then have a closed position. FIG. 11 illustrates the position and shape of the blades 15 when they are partially outside the tube 11. In FIGS. 12 and 13, the blades 15 are entirely outside the tube 11 and take on their deployed position.

The passage from the closed position to the partially or fully deployed position or vice versa is done by moving the fastener element 31 by means of the rod 17. This rod advantageously comprises a threaded zone cooperating with a thread of this fastener element 31. A passage 32 is also provided between the tube 11 and the fastener element 31, this passage 32 allowing the filling of the vertebral cavity with a consolidation product.

When using the spacer of the invention to position two vertebra parts, this spacer 10 is inserted into the patient's body so that the spacer module 12 is placed inside the vertebra whose position needs to be changed. The distal end 21 of the spacer tube remains outside the patient.

Generally, the spacer is introduced into the vertebra by a pedicle, according to an angle which varies depending on which vertebra is treated and which may also depend on the morphology or the pathology of the patient.

In general, the angle between the spacer and a theoretical axis coinciding with the patient's spine is of the order of 20°, generally between 10° and 30°.

When the spacer 10 is placed in the vertebra to be consolidated, it is first positioned and oriented according to the places in which forces must be applied and the desired orientation of these forces. During this positioning, the blades 15 are in a closed position, as illustrated by FIGS. 5 and 10. It is possible to choose the places where the blades will apply a force by choosing the orientation of the spacer module 12, which can be done by pivoting the rod 17 by means of the handle 16.

The asymmetrical configuration of the blades makes it possible to treat anterior fractures and posterior fractures differently. Indeed, the orientation of the spacer module 12 may be modified to change the locations where the blades 15 will apply a force, to take into account the type, shape and position of the fracture.

When the spacer module 12 is placed inside the vertebra, the blades 15 are out of the tube 11 so as to act on the plates of the vertebra.

In the embodiment of FIGS. 1 to 8, when the spacer module 12 is placed in the patient's body, in the desired position, the handle 16 is actuated to rotate the rod 17 in the nut 19. This has the effect of moving the nut 19 towards the shoulder 20 and thus of shortening the distance between the two holding zones 14a, 14b of the spacer module 12. The blades 15 then deploy and take an arched shape. The amplitude of displacement of the blades can be controlled as a function of the displacement amplitude of the rod 17. This makes it possible to control the spreading force applied to the vertebral plates.

In the embodiment of FIGS. 9 to 13, wherein the blades are made of a shape memory alloy, the spacer 10 is inserted into the body of the patient while the spacer module 12 is arranged inside the tube, as shown in FIG. 10. This can be done while the shape memory alloy is in its martensitic phase or when the alloy has already reached the austenitic transformation temperature.

When the spacer has reached the desired position, the rod 17 is advanced relative to the tube 11 to move the spacer module 12 outside of the tube. This makes it possible to release the blades 15, so as to reach a partially deployed position as illustrated by FIG. 11, and then a deployed position as illustrated by FIG. 12. By their shape memory alloy composition and by their arched shape when these blades are at a temperature corresponding to the temperature of the human body, these blades 15 apply a certain spreading force. The advantage of using a shape memory alloy is the fact that, when this alloy is in austenitic phase, the blades can apply a particularly large force with respect to their dimension.

The manipulation of the handle 16 makes it possible to choose how far the spacer module 12 protrudes from the tube 11 and consequently how far the blades extend from the tube. This makes it possible to manage the shape of the blades and consequently the spreading force and the amplitude of the movement that these blades apply to the parts of the vertebra with which they are in contact.

When the spacer 10 has moved the two vertebra elements to the desired position, a consolidation material such as a resin or an acrylic cement, for example, is introduced into the tube 11. This material is pushed from the distal end 21 of the tube towards the spacer module 12. This material leaves the tube through the opening or openings 24 and fills the cavity disposed between the vertebral plates. This material then solidifies and secures the vertebral plates in the desired position, defined by the spacers. The spacer module 12 remains in place in the vertebra, while the other elements of the spacer are removed from the patient by unscrewing the rod 17.

With regard to consolidation materials, it is possible to use conventional materials such as cement or acrylic resins or other biocompatible materials, which harden after injection. It is also possible to use materials which reform in a structure similar to a bone structure. Such a material may, for example, contain stem cells.

In the two embodiments described, that is to say in the embodiment illustrated by FIGS. 1 to 8 as well as in the embodiment illustrated by FIGS. 9 to 13, the rod can be locked in position by means of a locking device (not shown). This locking device makes it possible to ensure that the spacer module remains in the position in which it was placed, during the operation. This locking device can take different forms such as a nut, an element having an eccentric or any other suitable means acting on the portion of the rod which is outside the body of the patient during the operation.

It is possible to have a set of spacer modules 12 having different sizes, different shapes, being provided to apply different forces or having other different characteristics. The choice of the spacer module can be made according to the characteristics of the patient, the type of fracture, the forces to be applied or other parameters.

The present invention makes it possible to precisely choose the places to which the spreading forces are applied, this in particular thanks to the asymmetry of the blades. It is also possible to precisely choose the force applied by the blades, thanks to the adjustment of the actuator. The use of a shape memory alloy is particularly suitable for this application because these alloys are able to generate significant forces when the alloy is in the austenitic phase, for small blades.

The opening or openings 24 for the injection of filler materials may be large relative to the tube, allowing a relatively simple and fast filling.

In addition, the mechanical parts forming the spacer are relatively uncomplicated and do not require extremely precise machining of a large number of parts. This implies a lower manufacturing cost as well as increased reliability.

The invention claimed is:

1. A spacer system, a part of which is intended to be introduced in a fractured or defective vertebra, the spacer system comprising:
    a tube;
    a spacer module for introducing into said vertebra; and
    an actuating system of the spacer module, the actuating system comprising at least one rod which is accessible from a distal end of the tube and connected to said spacer module wherein the spacer module comprises two blades coplanar to a longitudinal axis of the rod, the two blades being movable between a closed position in which the blades are substantially parallel to the longitudinal axis of the rod, and a deployed position in which the blades have an arched shape for exerting a spreading force on parts of the vertebra with which the blades are in contact, the rod having a channel, a first end of the channel being in fluid communication with a distal end of the tube and a second end the channel being in fluid communication with an opening near the blades, the channel being configured to allow a consolidation material to be pushed from the tube through the channel and out of the opening where it can solidify to secure the parts of the vertebra, and wherein the two blades are asymmetrical with respect to each other and with respect to said longitudinal axis of the rod in their deployed position.

2. The spacer system of claim 1, wherein the arched shape of each of the blades in the deployed position defines at least one apex having a tangent parallel to the longitudinal axis of the rod, and wherein a straight line connecting the apexes of the opposing blades form an angle with a plane perpendicular to the longitudinal axis of the rod, this angle being greater than or equal to 5° and less than or equal to 30°.

3. The spacer system of claim 2, wherein the angle is greater than or equal to 15° and less than or equal to 25°.

4. The spacer system of claim 1, wherein at least one of the blades has more than one apex having a tangent parallel to the longitudinal axis of the rod.

5. The spacer system of claim 4, wherein at least one straight line connecting one of the apexes of one of the blades with an apex of the opposite blade forms an angle with a plane perpendicular to the longitudinal axis of the rod, this angle being greater than or equal to 5° and less than or equal to 30°.

6. The spacer system of claim 4, wherein the angle is greater than or equal to 15° and less than or equal to 25°.

7. The spacer system of claim 4, wherein at least one of the blades has an apex zone, the apex zone being a rectilinear zone parallel to the longitudinal axis of the rod and whose distance to the rod is a maximum when the blades are in their deployed position.

8. The spacer system of claim 7, wherein a straight line connecting a middle of the apex zones of the opposed blades forms an angle with a plane perpendicular to the longitudinal axis of the rod, this angle being greater than or equal to 5° and less than or equal to 30°.

9. The spacer system of claim 1, wherein the spacer module is detachable from the rod.

10. The spacer system of claim 1, wherein the opening into at least one opening is between the blades.

11. The spacer system of claim 1, wherein the channel is formed between the rod and the tube.

12. The spacer system of claim 1, wherein the spacer module has two holding zones for the blades, and a nut cooperating with a threaded proximal end of the rod.

13. The spacer system of claim 12, wherein the blades are integral with a proximal holding zone which is fixed relative to the rod and with a distal holding zone movable relative to the rod by means of the nut, and wherein the positioning of the blades is achieved by moving the nut by means of the threaded proximal end of the rod.

14. The spacer system of claim 1, wherein the blades are made of a shape memory alloy.

15. The spacer system of claim 14, wherein the blades have an arched shape in the absence of external stresses when the shape memory alloy is in the austenitic phase.

16. The spacer system of claim 14, wherein the blades have a substantially rectilinear shape in the absence of external stresses when the shape memory alloy is in the martensitic phase.

17. The spacer system of claim 14, wherein the shape memory alloy has a transition temperature between the martensitic phase and the austenitic phase of between 0° C. and 37° C.

18. The spacer system of claim 1, wherein the blades are secured to a blade fastener element connected to a rod.

19. The spacer system of claim 18, wherein the rod is accessible from outside the patient and is arranged to move the blades between a position in which the blades are entirely placed in the tube and a position in which the blades are entirely placed outside the tube.

20. The spacer system of claim 1, further comprising a locking device configured to lock the rod in a defined position relative to the tube.

* * * * *